US011020420B2

(12) United States Patent
Nakamoto et al.

(10) Patent No.: US 11,020,420 B2
(45) Date of Patent: Jun. 1, 2021

(54) BIOCOMPATIBLE PERITONEAL DIALYSATE

(71) Applicant: TERUMO KABUSHIKI KAISHA, Tokyo (JP)

(72) Inventors: Hidetomo Nakamoto, Tokyo (JP); Hirokazu Okada, Tokyo (JP); Shinji Oomori, Tokyo (JP); Yuri Jinnouchi, Kanagawa (JP); Hiroshi Nishitani, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 68 days.

(21) Appl. No.: 16/308,215

(22) PCT Filed: Jun. 9, 2017

(86) PCT No.: PCT/JP2017/021496
§ 371 (c)(1),
(2) Date: Dec. 7, 2018

(87) PCT Pub. No.: WO2017/213256
PCT Pub. Date: Dec. 14, 2017

(65) Prior Publication Data
US 2019/0262380 A1    Aug. 29, 2019

(30) Foreign Application Priority Data

Jun. 9, 2016  (JP) .............. JP2016-115736

(51) Int. Cl.
*A61K 31/715* (2006.01)
*A61P 7/08* (2006.01)
(Continued)

(52) U.S. Cl.
CPC ............... *A61K 31/715* (2013.01); *A61J 1/10* (2013.01); *A61J 1/2093* (2013.01);
(Continued)

(58) Field of Classification Search
CPC ....... A61K 31/715; A61K 9/0019; A61P 7/08; A61J 1/10; A61J 1/2093
(Continued)

(56) References Cited

U.S. PATENT DOCUMENTS

2004/0060865 A1    4/2004  Callan et al.
2004/0121982 A1    6/2004  Martis et al.
(Continued)

FOREIGN PATENT DOCUMENTS

EP    2 926 835 A1    10/2015
EP    2 926 836 A1    10/2015
(Continued)

OTHER PUBLICATIONS

The Extended European Search Report dated Apr. 24, 2019, by the European Patent Office in corresponding European Patent Application No. 17810428.7-1114. (6 pages).
(Continued)

*Primary Examiner* — Phillip A Gray
(74) *Attorney, Agent, or Firm* — Buchanan Ingersoll & Rooney PC

(57) ABSTRACT

A biocompatible peritoneal dialysate according to the present invention is a sterilized biocompatible peritoneal dialysate composed of an acidic first solution containing icodextrin and a second solution containing a pH adjuster, wherein the pH after mixing of the sterilized first solution with the sterilized second solution is 6.0 to 7.5.

14 Claims, 1 Drawing Sheet

(51) Int. Cl.

| | |
|---|---|
| *A61J 1/10* | (2006.01) |
| *A61J 1/20* | (2006.01) |
| *A61K 9/00* | (2006.01) |
| *A61K 9/08* | (2006.01) |
| *A61K 33/14* | (2006.01) |
| *A61M 1/28* | (2006.01) |
| *A61K 47/36* | (2006.01) |
| *A61K 47/02* | (2006.01) |
| *A61K 47/12* | (2006.01) |

(52) U.S. Cl.
CPC ............... *A61K 9/0019* (2013.01); *A61K 9/08* (2013.01); *A61K 33/14* (2013.01); *A61K 47/02* (2013.01); *A61K 47/12* (2013.01); *A61K 47/36* (2013.01); *A61M 1/28* (2013.01); *A61P 7/08* (2018.01)

(58) Field of Classification Search
USPC .......................................................... 604/29
See application file for complete search history.

(56) References Cited

U.S. PATENT DOCUMENTS

| | | | |
|---|---|---|---|
| 2006/0128658 A1 | 6/2006 | Martis et al. | |
| 2015/0231321 A1* | 8/2015 | Nishitani | A61J 1/10 604/410 |

FOREIGN PATENT DOCUMENTS

| | | |
|---|---|---|
| JP | 2000051348 A | 2/2000 |
| JP | 2007524629 A | 8/2007 |
| JP | 2010150281 A | 7/2010 |
| JP | 2014050577 A | 3/2014 |
| JP | 2015-218141 A | 12/2015 |
| WO | 2014083613 A1 | 6/2014 |

OTHER PUBLICATIONS

International Search Report (with English Translation) and Written Opinion issued in corresponding International Patent Application No. PCT/JP2017/021496, 9 pages, dated Jul. 11, 2017.
Conti et al. "Glycated Adducts Induce Mesothelial Cell Transdifferentiation: Role of Glucose and Icodextrin Dialysis Solutions," Journal of Nephrology, 2008 (month unknown), vol. 21, No. 3, pp. 426-437.
Lei et al., "Poly (ADP-ribose) Polymerase-1 in high Glucose-Induced Epithelial-Mesenchymal Transition During Peritoneal Fibrosis," International Journal of Molecular Medicine, 2012 (month unknown), vol. 29, No. 3, pp. 472-478.
Terabayashi et al., "Vascular Endothelial Growth Factor Receptor-3 is a Novel Traget to Improve Net Ultrafiltration in Methylglyoxal-Induced Peritoneal Injury," Laboratory Investigation, 2015 (month unknown), vol. 95, No. 9, pp. 1029-1043.
Office Action (Communication pursuant to Article 94(3) EPC) dated Nov. 3, 2020, by the European Patent Office in corresponding European Patent Application No. 17 810 4281-1112. (5 pages).

* cited by examiner

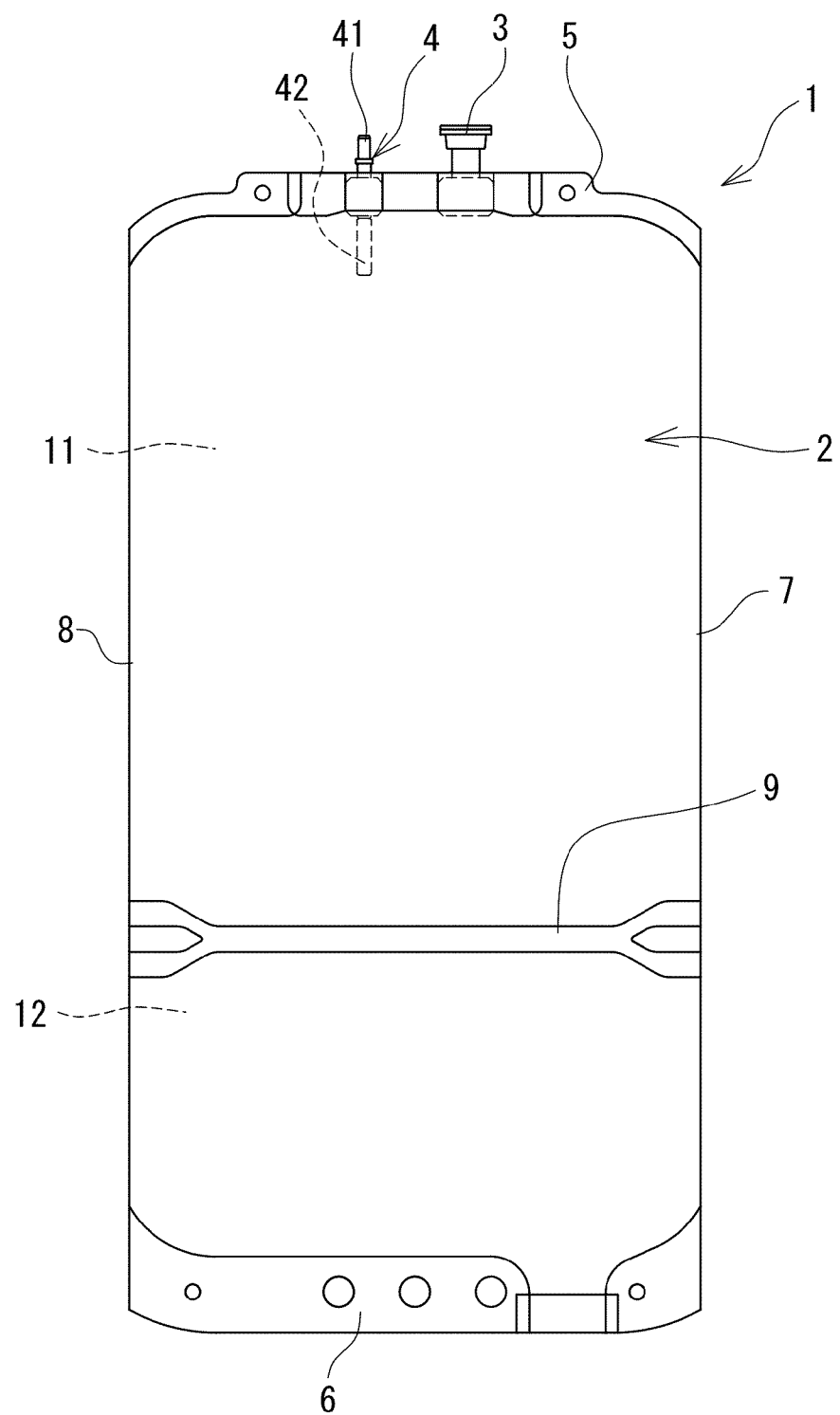

BIOCOMPATIBLE PERITONEAL DIALYSATE

TECHNICAL FIELD

The present invention relates to a peritoneal dialysate having a neutral pH at the time of administration, containing icodextrin, and having excellent biocompatibility.

BACKGROUND ART

Peritoneal dialysis therapy as one of symptomatic treatments for a renal failure does not require large-scale equipment and instruments, and has little temporal restraint, compared with dialysis therapy performed by an artificial kidney. For this reason, the peritoneal dialysis therapy is attracting attention as a kind of home medical care. Many peritoneal dialysates which are currently in use have used glucose as an osmotic substance. The glucose has an advantage of being relatively safe and cheap. However, because the glucose has a small molecular weight, it is rapidly absorbed through a peritoneum, so a sustained water removal effect cannot be obtained. Due to the above situations, a search for an osmotic substance capable of maintaining ultrafiltration during long-term storage in place of the glucose was conducted. It has been found that icodextrin, which is a glucose polymer, is suitable for the peritoneal dialysate.

Since the icodextrin has a large molecular weight, it is not rapidly absorbed through the peritoneum. The icodextrin mainly acts as a colloid osmotic substance and can obtain the water removal effect while maintaining an osmotic pressure with blood plasma. Currently, the peritoneal dialysate using the icodextrin is prescribed so that a chemical solution is in the range of pH 5.0 to 5.5 in order to prevent decomposition and coloration of the icodextrin.

Recent studies have reported that a peritoneal dialysate with such a pH substantially reduces an immune defense mechanism of peritoneal macrophage and increases a risk of peritonitis due to bacterial penetration. In addition, there are also reports of prolonged fever/abdominal pain during an introduction of continuous peritoneal dialysis therapy, and the abdominal pain occurs at the time of injecting the dialysate. In addition, it has been reported that a peritoneal dialysate having a pH of 5.0 to 5.5 has a remarkably high disability to cultured peritoneal mesothelial cells.

However, the pH of the peritoneal dialysate has a great influence on stability of the icodextrin. When the pH of the peritoneal dialysate is increased, the glucose is produced from the icodextrin during manufacturing and storage. The peritoneal dialysate is colored due to the deterioration of the produced glucose, and thus the product value is remarkably lowered. That is, an absorbance at 284 nm, which is an index of 5-hydroxymethylfurfural as a main decomposition product of the glucose, is continuously increased. In addition, when the pH of the peritoneal dialysate is increased, the absorbance at 228 nm, which is an index of 3-deoxyglucosone as the main decomposition product of the glucose, is also increased depending on the pH.

Therefore, as a method of increasing a pH of a peritoneal dialysate while suppressing decomposition/coloration of icodextrin, a formulation separately accommodating icodextrin and a chemical solution component having a high pH until the icodextrin and the chemical solution component are used and aseptically mixing the icodextrin and the chemical solution component immediately before the icodextrin and the chemical solution component are used (JP-2010-150281 A (WO 2004-058277 A)) has been developed.

However, the demand for stability of the peritoneal dialysate and safety of the peritoneal dialysate has been increasing more and more in recent years, and an emergence of a peritoneal dialysate having a physiological pH that does not adversely affect a human body more than ever, suitably suppressing a glucose decomposition product produced from the icodextrin or coloration more than ever, and having excellent biocompatibility has been demanded.

CITATION LIST

Patent Literature

Patent Literature 1: JP-2010-150281 A (WO 2004-058277 A)

SUMMARY OF INVENTION

Technical Problem

The present invention provides a peritoneal dialysate capable of improving stability of icodextrin during heating sterilization and subsequent storage as much as possible, having a pH close to a physiological region, and having excellent biocompatibility.

Solution to Problem

The above object is achieved by the following present invention.

A biocompatible peritoneal dialysate according to the present invention is a sterilized biocompatible peritoneal dialysate composed of an acidic first solution containing icodextrin and a second solution containing a pH adjuster, in which the pH after mixing of the sterilized first solution with the sterilized second solution is 6.0 to 7.5 and an expression of biomarkers for fibrosis, angiogenesis, and epithelial mesenchymal transition is small.

BRIEF DESCRIPTION OF DRAWINGS

FIG. 1 is a front view of a medical bag in which a dialysate of the present invention is received.

DESCRIPTION OF EMBODIMENTS

Hereinafter, a peritoneal dialysate of the present invention will be described in detail.

The peritoneal dialysate of the present invention is mainly composed of a first solution containing icodextrin and a second solution not containing icodextrin and having an alkaline region from a neutral region, and is a 2-liquid type peritoneal dialysate in which the first solution and the second solution are mixed immediately before being used. In addition, the peritoneal dialysate has a pH of 6.0 to 7.5, and preferably 6.2 to 6.8, after the first solution and the second solution are mixed.

In the peritoneal dialysate of the present invention, a content of the icodextrin in the first solution is 76.0 to 94.0 g/L, and preferably 84.0 to 94.0 g/L. When the content of the icodextrin is less than 76.0 g/L, there is a possibility that water removal does not occur and appropriate dialysis may not be expected in the peritoneal dialysis after the first solution and the second solution are mixed. In addition, when the content of the icodextrin contained in the first solution exceeds 94.0 g/L, the amount of glucose decomposition product produced from the icodextrin is increased, which is not preferable. This makes it possible to suitably suppress the glucose decomposition product produced from the icodextrin during heating sterilization and subsequent storage, and to realize a biocompatible peritoneal dialysate excellent in safety and storage property.

A content of sodium chloride in the first solution is 1.89 to 2.37 g/L, and preferably 2.00 to 2.37 g/L. The sodium chloride is blended for the purpose of adjusting an osmotic pressure. When the content of the sodium chloride in the first solution exceeds 2.37 g/L, the amount of glucose decomposition product produced from the icodextrin is increased, and the peritoneal dialysate having excellent biocompatibility cannot be realized, which is not preferable.

In the peritoneal dialysate of the present invention, from the viewpoint of suppressing the glucose decomposition product produced from the icodextrin, the first solution does not contain a pH adjuster such as lactic acid, sodium lactate, and sodium hydroxide. In addition, the first solution does not contain potassium and its salt, or magnesium and its salt.

In the peritoneal dialysate of the present invention, the pH of the sterilized first solution is an acidic region, and specifically, preferably has a pH of 4.0 to 6.5, and more preferably pH of 4.0 to 6.0. When the pH is less than 4.0, the amount of 5-hydroxymethylfurfural, which is a glucose decomposition product produced from the icodextrin, is increased, and the biocompatible peritoneal dialysate cannot be realized, which is not preferable.

In the peritoneal dialysate of the present invention, the sterilized second solution is an alkaline region from a neural region, and specifically, preferably has a pH of 6.0 to 8.0, and more preferably pH of 6.2 to 7.2. When the pH is less than 6.0 or exceeds 8.0, the pH after the mixing is not in the range of 6.0 to 7.5, and the biocompatible peritoneal dialysate in which the expression level of biomarkers for fibrosis, angiogenesis, and epithelial mesenchymal transition in the peritoneum is small cannot be realized, which is not preferable.

In the peritoneal dialysate of the present invention, the pH after the mixing of the sterilized first solution with the sterilized second solution (mixed solution) is 6.0 to 7.5. In the case where the pH after the mixing (mixed solution) is less than 6.0, there is a possibility that an immune defense mechanism of macrophage is lowered, disability to peritoneal mesothelial cells is high, and the expression level of biomarkers for fibrosis, angiogenesis, and epithelial mesenchymal transition in the peritoneum is increased. In addition, when the pH after mixing (mixed solution) exceeds 7.5, an adverse effect on a living body is likely to occur and the biocompatible peritoneal dialysate cannot be realized, which is not preferable.

In the present invention, the second solution contains a pH adjuster. As the pH adjuster, lactic acid or lactate may be used. In addition, as the lactate, sodium lactate and the like may be used.

In the present invention, the second solution contains at least one of sodium chloride, sodium lactate, calcium chloride, and magnesium chloride. The amount of these components is not particularly limited, and only has to be the same as that of the usual peritoneal dialysate, and is preferably 16.6 to 347.8 g/L of sodium chloride, 21.3 to 448.0 g/L of sodium lactate, 1.22 to 25.7 g/L of calcium chloride, and 0.24 to 5.10 g/L of magnesium chloride.

In the present invention, if necessary, an alkaline pH adjuster such as sodium hydroxide may be used for performing a pH preparation in order to adjust the second solution to be alkaline. A dosage of the pH adjuster is an amount which adjusts the pH of the peritoneal dialysate to be a pH of 6.0 to 7.5 after the mixing of the sterilized first solution with the sterilized second solution.

From the viewpoint of suppressing the amount of glucose decomposition product produced from the icodextrin, these components are blended in the second solution, which does not contain the icodextrin, except for the sodium chloride.

In the peritoneal dialysate of the present invention, the first solution and the second solution are separately filled and packaged in a container made of polypropylene, polyvinyl chloride, or the like, sterilized, and aseptically mixed immediately before being used.

In particular, the peritoneal dialysate of the present invention is received in a medical bag having a first chamber and a second chamber formed by being separated by a partitioning means capable of opening the inside thereof, in which it is preferable that the first chamber is provided with a discharge port through which the inside and the outside of the medical bag communicate with each other and separately receives the first solution and the second solution. At this time, it is preferable that the first solution is received in the first chamber and the second solution is received in the second chamber. In this way, even if the solution is administered without mixing the first solution and the second solution, it is possible to administrate the first solution, which is relatively safe in terms of an osmotic pressure.

In addition, the medical bag (medical container) 1 in which the dialysate of the present invention is received is a medical bag which contains a flexible bag and a dialysate composed of the aforementioned biocompatible peritoneal dialysate received in a flexible bag 2. The flexible bag 2 has a first chamber 11 and a second chamber 12 formed by being separated by a partitioning means capable of opening the inside thereof, and the first chamber 11 is provided with a discharge port 4 through which the inside and outside of the flexible bag 2 communicate with each other and the aforementioned first solution is received in the first chamber 11 and the aforementioned second solution is received in the second chamber.

An openable partitioning means includes a heat seal which can be broken by a solution pressure of the received first solution or second solution when one of the first chamber and the second chamber is pressed. By doing so, it is possible to easily perform the mixing of the first solution with the second solution. Specifically, as the flexible bag 2, a container of Midpeliq (registered trademark) (manufactured by Terumo Corporation) may be used.

In the present invention, a sterilization method includes an autoclave sterilization (high pressure steam sterilization). The conditions are 110 to 130° C. for 25 to 45 minutes, and preferably 115 to 125° C. for 30 to 40 minutes.

In general, the peritoneal dialysate of the present invention is externally packaged with an oxygen permeable membrane material such as a three-layer film made of polypropylene-polyamide-polypropylene. In order to prevent the dialysate in the container from deteriorating, it may be further externally packaged with the oxygen impermeable membrane material.

Examples of the oxygen impermeable membrane material include a three-layer laminate film containing an ethylene-vinyl alcohol copolymer film, a polyvinyl alcohol film, a polyvinylidene chloride film or the like as an intermediate layer (for example, a laminated film whose outer layer is made of a polyester film, a stretched nylon film, a stretched polypropylene film or the like and inner layer is made of an unstretched polypropylene film), a laminated film containing an aluminum layer (for example, a laminated film made of polyester film-aluminum layer-unstretched polypropylene film), and a laminated film including an inorganic deposition film (for example, a laminated film composed of polyester film-silicon deposited film-unstretched polypropylene film, stretched nylon film-silicon deposited film-unstretched polypropylene film, polyester film-aluminum deposited film-unstretched polypropylene film, and alumina deposited polyester film-polyvinylidene chloride film-unstretched polypropylene film) and the like.

As the medical bag (medical container) 1 containing the dialysate, for example, the medical bag as shown in FIG. 1 can be suitably used.

The medical bag (medical container) 1 of this embodiment is provided with the flexible bag 2, and the flexible bag 2 is provided with the partitioning means (weak seal portion) 9 for partitioning the inside thereof into two. The inside of the flexible bag 2 is partitioned into the first chamber 11 and the second chamber 12 by the partitioning means (weak seal portion) 9. Further, the medical bag 1 is provided with the discharge port 4 communicating with the first chamber 11 and a mixed injection port 3. In addition, the medical bag 1 includes a first seal portion 5 (more specifically, the upper seal portion 5 formed above the upper first chamber 11) for sealing one end portion of the flexible bag 2 and a second seal portion 6 (specifically, a lower seal portion 6 formed under the second chamber 12) for sealing the other end portion of the flexible bag 2. In addition, a side portion 7 and a side portion 8 of the medical bag 1 are folded portions of a sheet forming the flexible bag 2.

In addition, in this embodiment, the discharge port 4 is provided on the side of the first chamber 11. Similarly, the mixed injection port 3 is also provided on the side of the first chamber 11. Specifically, the discharge port 4 and the mixed injection port 3 are fixed to the upper seal portion 5, and are communicable with the side of the first chamber 11. In addition, in this embodiment, a port member 41 having a connector portion for connection to a tube is fixed to the discharge port 4 in a liquid-tight manner. In addition, the port member 41 is closed in a non-ruptured state, and has a communicable member 42 that communicates by rupture. By bending this communicable member 42 from the outside of the medical bag 1, the inside of the port member 41 and the inside of the first chamber 11 communicate with each other to be able to discharge a liquid. It is preferable that the aforementioned first solution is received in the first chamber 11 and the aforementioned second solution is received in the second chamber 12.

The partitioning means (weak seal portion 9) has seal strength enough to be peeled by pressing the medical bag 1 with a finger, a palm or the like, gripping the medical bag 1 so as to squeeze one of the drug chambers, or the like in a state in which the medical bag 1 is filled with a liquid. The first chamber 11 and the second chamber 12 communicate with each other by opening (specifically, peeling) the partitioning means (weak seal portion 9) to mix the sterilized first solution with the sterilized second solution.

The flexible bag 2 is made of a flexible synthetic resin. Examples of the flexible bag 2 may include a flexible bag formed into a tubular shape by an inflation molding method, a flexible bag manufactured by various methods such as a T die method, a blow molding method, a dry laminating method, a hot melt laminating method, a coextrusion inflation method, a coextrusion T die method, and a hot press method.

The flexible bag 2 preferably has a gas barrier property. As a degree of the gas barrier property, water vapor permeability is preferably 50 g/m²·24 hrs·40° C.·90% RH or less, more preferably 10 g/m²·24 hrs·40° C.·90% RH or less, and still more preferably 1 g/m²·24 hrs·40° C.·90% RH or less.

Although the peritoneal dialysate of the present invention has been described in detail, the present invention is not limited thereto, and various improvements and changes may be made without departing from the gist of the present invention.

EXAMPLES

Hereinafter, the present invention will be described in more detail with reference to specific examples of the present invention. It is to be noted that the present invention is not limited to the following examples.

Example 1

A first solution was prepared by dissolving 150.0 g of icodextrin and 3.745 g of sodium chloride in 1680 mL of water for injection. In addition, a second solution was prepared by dissolving 6.955 g of sodium chloride, 8.960 g of sodium lactate, 0.5140 g of calcium chloride, and 0.1016 g of magnesium chloride·hexahydrate in 320 mL of water for injection.

As the flexible bag, a multi-chamber container made of polypropylene [Midpeliq (registered trademark) (manufactured by Terumo Corporation)] was prepared. 1680 mL of the first solution was filled in the first chamber provided with the discharge port of the multi-chamber container and 320 mL of the second solution was filled in the second chamber. The multi-chamber container filled with a liquid was provided in a three-way bag made of polypropylene/nylon/polypropylene and deaerated and packaged. Thereafter, the heating sterilization (121° C., 30 minutes) was performed using an autoclave.

The pHs of the sterilized first solution and second solution and the mixed solution (peritoneal dialysate) were measured. The pH of the first solution was 4.9, the pH of the second solution was 6.9, and the pH of the mixed solution was 6.5. 50 mL of the mixed solution was subjected to an animal experiment for quantifying a biomarker in peritoneum.

Example 2

A first solution was prepared by dissolving 156.0 g of icodextrin and 3.745 g of sodium chloride in 1680 mL of water for injection. In addition, a second solution was prepared by dissolving 6.955 g of sodium chloride, 8.960 g of sodium lactate, 0.5140 g of calcium chloride, and 0.1016 g of magnesium chloride·hexahydrate in 320 mL of water for injection. 840 mL of the first solution and 160 mL of the second solution were filled, heated, and sterilized under the same conditions as the Example 1. The pHs of the sterilized first solution and second solution and the mixed solution (peritoneal dialysate) were measured. The pH of the first solution was 4.8, the pH of the second solution was 7.0, and the pH of the mixed solution was 6.4.

Example 3

A first solution was prepared by dissolving 142.0 g of icodextrin and 3.745 g of sodium chloride in 1680 mL of water for injection. In addition, a second solution was prepared by dissolving 6.955 g of sodium chloride, 8.960 g of sodium lactate, 0.5140 g of calcium chloride, and 0.1016 g of magnesium chloride·hexahydrate in 320 mL of water for injection. 1680 mL of the first solution and 320 mL of the second solution were filled, heated, and sterilized under the same conditions as the Example 1. The pHs of the sterilized first solution and second solution and the mixed solution (peritoneal dialysate) were measured. The pH of the first solution was 5.0, the pH of the second solution was 6.9, and the pH of the mixed solution was 6.5.

Comparative Example 1

A solution in which 1 mol/L of hydrochloric acid was added to 50 mL of the mixed solution of the first solution and the second solution at a ratio of 95 µL in the Example was prepared. In this case, the pH was 5.0. This mixed solution adjusted to pH 5.0 was subjected to an animal experiment for quantifying the biomarker in peritoneum.

Comparative Example 2

150.0 g of icodextrin and 3.745 g of sodium chloride were dissolved in 1680 mL of water for injection and pH was adjusted with hydrochloric acid to prepare a first solution. In addition, a second solution was prepared by dissolving 6.955 g of sodium chloride, 8.960 g of sodium lactate, 0.5140 g of calcium chloride, and 0.1016 g of magnesium chloride·hexahydrate in 320 mL of water for injection. 1680 mL of the first solution and 320 mL of the second solution were filled, heated, and sterilized under the same conditions as the Example 1. The pHs of the sterilized first solution and second solution and the mixed solution (peritoneal dialysate) were measured. The pH of the first solution was 4.0, the pH of the second solution was 7.0, and the pH of the mixed solution was 5.0.

(Quantization of Biomarker in Peritoneum)

As an animal, rats (Crj: CD (SD), 7 weeks old, n=4 in each group, male) were used. In this experiment, rats were supplied with sufficient amounts of food and water, attention was sufficiently paid to hygiene environment, attention was paid not to cause peritonitis due to bacterial infection. The aseptically prepared dialysate of the Examples or the Comparative Examples were heated to 37° C. in advance, and continuously administered into an abdominal cavity at 40 mL/kg once a day for 40 days. The dialysate was administered under anesthesia to prevent rats from feeling pain.

A parietal peritoneum was collected on the 41st day after the start of administration in each group and the expression level of the biomarker of the peritoneum was quantized by real-time PCR (TaqManprobe method). CCN2/ctgf, TGF-β1, fibronectin, and collagen I as biomarkers for fibrosis, Tie2 and VEGF as biomarkers for angiogenesis, Snail 1 and Twist 1 as biomarkers for epithelial mesenchymal transition, and GAPDH as a biomarker for endogenous control were selected as targets, and the expression levels of these targets were measured.

The relative expression levels of each biomarker in the peritoneum corrected by the GAPDH as a biomarker of the endogenous control are shown in Tables 1 and 2. The expression levels of the biomarkers of the fibrosis, the angiogenesis, and the epithelial mesenchymal transition of the Example 1 were smaller than those of the Comparative Example 1, and the biocompatibility of the Example 1 was more excellent than that of the Comparative Example 1. This could not be predicted from the prior art.

TABLE 1

| Example | Relative expression level of biomarker in peritoneum corrected by GAPDH (targeted expression level of biomarker/expression level of GAPDH) | | | |
|---|---|---|---|---|
| | CCN2/ctgf | TGF-β1 | Fibronectin | Collagen I |
| Example 1 | $8.01 \times 10^{-3}$ | $1.45 \times 10^{-3}$ | $3.06 \times 10^{-2}$ | $3.32 \times 10^{-2}$ |
| Comparative Example 1 | $1.54 \times 10^{-2}$ | $1.79 \times 10^{-3}$ | $3.49 \times 10^{-2}$ | $4.32 \times 10^{-2}$ |

TABLE 2

| Example | Relative expression level of biomarker in peritoneum corrected by GAPDH (targeted expression level of biomarker/expression level of GAPDH) | | | |
|---|---|---|---|---|
| | Tie2 | VEGF | Snail1 | Twist1 |
| Example 1 | $2.62 \times 10^{-3}$ | $1.55 \times 10^{-2}$ | $1.48 \times 10^{-4}$ | $7.01 \times 10^{-3}$ |
| Comparative Example 1 | $3.76 \times 10^{-3}$ | $1.87 \times 10^{-2}$ | $3.96 \times 10^{-4}$ | $1.10 \times 10^{-2}$ |

(Temporal Change Test)

For the first solutions of the Example 1, Example 2, Example 3 and the Comparative Example 2, a temporal change of absorbance at 284 nm, which is an index of 5-hydroxymethylfurfural as a main glucose decomposition product, was measured. The results are shown in Table 3. The peritoneal dialysates of the Example 1, Example 2, Example 3, and the Comparative Example 2 were stored in a constant temperature bath at 60° C., and the absorbance of the first solutions was measured.

TABLE 3

| Days | Example 1 | Example 2 | Example 3 | Comparative Example 2 |
|---|---|---|---|---|
| 0 day | 0.162 | 0.172 | 0.152 | 0.185 |
| 7 days | 0.268 | 0.277 | 0.236 | 0.303 |

As shown in the Table 3, compared with the Example 1, Example 2, and Example 3, Comparative Example 2 has a larger temporal change of the absorbance at 284 nm, which is an index of 5-hydroxymethylfurfural as the main glucose decomposition product.

The peritoneal dialysate of the present invention is a sterilized peritoneal dialysate which is composed of an acidic first solution containing 76.0 to 94.0 g/L of icodextrin and 1.97 to 2.37 g/L sodium chloride and an alkaline second solution containing an alkaline pH adjuster, in which the first solution does not contain the pH adjuster, the pH of the first solution immediately after the sterilization is 4.0 to 6.5, the pH of the sterilized second solution is 6.0 to 8.0, the pH after the mixing of the sterilized first solution with the sterilized second solution is 6.0 to 7.5, and the first solution and the second solution are sterilized under sterilization conditions of 110 to 130° C. for 25 to 45 minutes, so it is possible to realize the biocompatible peritoneal dialysate which produces less 5-hydroxymethylfurfural after the heating sterilization or after being stored for 7 days at 60° C. This could not be predicted from the prior art.

INDUSTRIAL APPLICABILITY

As described above in detail, the peritoneal dialysate of the present invention suppresses the glucose decomposition product produced from the icodextrin during the heating sterilization and the subsequent storage as much as possible while being in the pH physiological region, and thus can be used industrially as the biocompatible peritoneal dialysate which is extremely excellent in stability and has a small expression level of biomarkers of fibrosis, angiogenesis and epithelial mesenchymal transition in the peritoneum.

The biocompatible peritoneal dialysate of the present invention is as follows.

(1) In a biocompatible peritoneal dialysate composed of an acidic first solution containing icodextrin and a second solution containing a pH adjuster and sterilized, pH after mixing of the sterilized first solution with the sterilized second solution is 6.0 to 7.5 and an expression of biomarkers for fibrosis, angiogenesis, and epithelial mesenchymal transition is small.

The peritoneal dialysate of the present invention can suppress the temporal increase in the absorbance at 228 nm of the peritoneal dialysate to 284 nm, that is, greatly suppress the glucose decomposition product produced from the icodextrin during the heat sterilization and the subsequent storage, is excellent in stability and has less expression level of the biomarkers for the fibrosis, the angiogenesis, and the epithelial mesenchymal transition in the peritoneum, and has excellent biocompatibility.

(2) In the biocompatible peritoneal dialysate described in the above (1), the first solution contains 76.0 to 94.0 g/L of icodextrin, 1.89 to 2.37 g/L of sodium chloride, and does not contain the pH adjuster, the second solution contains the pH adjuster, the pH of the sterilized first solution is 4.0 to 6.5, the pH of the sterilized second solution is 6.0 to 8.0, the pH after the mixing of the sterilized first solution with the sterilized second solution is 6.0 to 7.5, and the first solution and the second solution are sterilized under the sterilization conditions of 110 to 130° C. for 25 to 45 minutes.

(3) In the biocompatible peritoneal dialysate described in the above (1) or (2), the second solution contains at least one of 16.6 to 347.8 g/L of sodium chloride, 21.3 to 448.0 g/L of sodium lactate, 1.22 to 25.7 g/L of calcium chloride, and 0.24 to 5.10 g/L of magnesium chloride.

The medical bag receiving the dialysate of the present invention is as follows.

(4) In a medical bag containing a flexible bag and a dialysate composed of the biocompatible peritoneal dialysate described in any one of the above (1) to (3) received in the flexible bag, the flexible bag has a first chamber and a second chamber formed by being separated by a partitioning means capable of opening the inside thereof, wherein the first chamber has a discharge port through which an inside and an outside of the flexible bag communicate with each other, the first solution is received in the first chamber, and the second solution is received in the second chamber.

The invention claimed is:

1. A biocompatible peritoneal dialysate composed of an acidic sterilized first solution containing icodextrin and a sterilized second solution containing a pH adjuster, wherein pH of the sterilized second solution is 6.0 to 6.2, and pH after mixing of the sterilized first solution with the sterilized second solution is 6.0 to 7.5 and an expression of biomarkers for fibrosis, angiogenesis, and epithelial mesenchymal transition is small.

2. The biocompatible peritoneal dialysate according to claim 1, wherein the first solution contains 76.0 to 94.0 g/L of icodextrin, 1.89 to 2.37 g/L of sodium chloride, and does not contain a pH adjuster, the pH of the sterilized first solution is 4.0 to 6.5, and the first solution and the second solution are sterilized under the sterilization conditions of 110 to 130° C. for 25 to 45 minutes.

3. The biocompatible peritoneal dialysate according to claim 1, wherein the second solution contains at least one of 16.6 to 347.8 g/L of sodium chloride, 21.3 to 448.0 g/L of sodium lactate, 1.22 to 25.7 g/L of calcium chloride, and 0.24 to 5.10 g/L of magnesium chloride.

4. A medical bag comprising a flexible bag and a dialysate composed of the biocompatible peritoneal dialysate according to claim 1 received in the flexible bag, wherein the flexible bag has a first chamber and a second chamber formed by being separated by a partitioning means capable of opening the inside thereof, the first chamber has a discharge port through which an inside and an outside of the flexible bag communicate with each other, the first solution is received in the first chamber, and the second solution is received in the second chamber.

5. A biocompatible peritoneal dialysate composed of an acidic sterilized first solution containing icodextrin and a sterilized second solution containing a pH adjuster, wherein pH of the sterilized first solution is 4.0 to 4.9, and pH after mixing of the sterilized first solution with the sterilized second solution is 6.0 to 7.5 and an expression of biomarkers for fibrosis, angiogenesis, and epithelial mesenchymal transition is small.

6. The biocompatible peritoneal dialysate according to claim 5, wherein the first solution contains 76.0 to 94.0 g/L of icodextrin, 1.89 to 2.37 g/L of sodium chloride, and does not contain a pH adjuster, the pH of the sterilized second solution is 6.0 to 8.0, and the first solution and the second solution are sterilized under the sterilization conditions of 110 to 130° C. for 25 to 45 minutes.

7. The biocompatible peritoneal dialysate according to claim 5, wherein the second solution contains at least one of 16.6 to 347.8 g/L of sodium chloride, 21.3 to 448.0 g/L of sodium lactate, 1.22 to 25.7 g/L of calcium chloride, and 0.24 to 5.10 g/L of magnesium chloride.

8. A medical bag comprising a flexible bag and a dialysate composed of the biocompatible peritoneal dialysate according to claim 5 received in the flexible bag, wherein the flexible bag has a first chamber and a second chamber formed by being separated by a partitioning means capable of opening the inside thereof, the first chamber has a discharge port through which an inside and an outside of the flexible bag communicate with each other, the first solution is received in the first chamber, and the second solution is received in the second chamber.

9. The biocompatible peritoneal dialysate according to claim 5, wherein pH of the sterilized second solution is 6.0 to 6.2.

10. The biocompatible peritoneal dialysate according to claim 1, wherein the second solution contains sodium chloride, sodium lactate, calcium chloride, and magnesium chloride.

11. The biocompatible peritoneal dialysate according to claim 5, wherein the second solution contains sodium chloride, sodium lactate, calcium chloride, and magnesium chloride.

12. The biocompatible peritoneal dialysate according to claim 5, wherein pH after mixing of the sterilized first solution with the sterilized second solution is 6.2 to 6.8.

13. The biocompatible peritoneal disalysate according to claim 1, wherein pH of the sterilized first solution is at least 4.0 and less than 4.7.

14. The biocompatible peritoneal disalysate according to claim 5, wherein pH of the sterilized first solution is at least 4.0 and less than 4.3.

\* \* \* \* \*